(12) United States Patent
Yoshida et al.

(10) Patent No.: US 10,264,957 B2
(45) Date of Patent: Apr. 23, 2019

(54) ENDOSCOPE LENS CLEANER

(71) Applicants: NAGASE MEDICALS CO., LTD., Osaka (JP); KYOTO PREFECTURAL PUBLIC UNIVERSITY CORPORATION, Kamigyo-ku, Kyoto-shi, Kyoto (JP)

(72) Inventors: Naohisa Yoshida, Kyoto (JP); Sae Ishii, Hyogo (JP); Atsushi Yumoto, Hyogo (JP); Hisami Yumoto, Hyogo (JP)

(73) Assignees: NAGASE MEDICALS CO., LTD., Osaka (JP); KYOTO PREFECTURAL PUBLIC UNIVERSITY CORPORATION, Kyoto (JP)

( * ) Notice: Subject to any disclaimer, the term of this patent is extended or adjusted under 35 U.S.C. 154(b) by 0 days.

(21) Appl. No.: 15/025,678

(22) PCT Filed: Sep. 29, 2014

(86) PCT No.: PCT/JP2014/075950
§ 371 (c)(1),
(2) Date: Mar. 29, 2016

(87) PCT Pub. No.: WO2015/046532
PCT Pub. Date: Apr. 2, 2015

(65) Prior Publication Data
US 2016/0235284 A1    Aug. 18, 2016

(30) Foreign Application Priority Data
Sep. 30, 2013   (JP) ................................ 2013-203998

(51) Int. Cl.
*A61B 1/00*    (2006.01)
*A61B 1/12*    (2006.01)
(Continued)

(52) U.S. Cl.
CPC .......... *A61B 1/126* (2013.01); *A61B 1/00089* (2013.01); *A61B 1/00091* (2013.01);
(Continued)

(58) Field of Classification Search
CPC ..... A61B 1/126; A61B 1/00091; A61B 1/018; A61B 1/00083; A61B 2017/00269; C11D 1/825; C11D 1/74; C11D 1/265
See application file for complete search history.

(56) References Cited

U.S. PATENT DOCUMENTS 4,056,481 A * 11/1977 Tate .................... C11D 3/18
510/347
4,436,653 A * 3/1984 Jacobsen .................. C11D 1/83
510/341
(Continued)

FOREIGN PATENT DOCUMENTS

JP    1-159808    11/1989
JP    7-89067    4/1995
(Continued)

OTHER PUBLICATIONS

International Search Report dated Oct. 28, 2014 in International Application No. PCT/JP2014/075950.
(Continued)

*Primary Examiner* — Timothy J Neal
(74) *Attorney, Agent, or Firm* — Wenderoth, Lind & Ponack, L.L.P.

(57) ABSTRACT

The present invention relates to a cleaner for an endoscope, the cleaner being used inside a living body during an endoscopic, surgical procedure. In particular, an object of the present invention is to reduce the burden on a physician and the patient during an endoscopic surgical procedure. The present invention therefore relates to a cleaner for cleaning debris from an endoscope and/or endoscopic accessories,
(Continued)

such as an endoscope lens and/or an endoscope hood (attachment), inside a living body. The present invention also relates to an antifoulant for antifouling treatment of an endoscope and/or endoscopic accessories. The antifoulant may comprise, for example, (i) a nonionic surfactant with an HLB of 1 to 11 and (ii) a nonionic surfactant with an HLB of 11 to 20.

5 Claims, 3 Drawing Sheets

(51) Int. Cl.
    *C11D 1/74*     (2006.01)
    *C11D 1/825*     (2006.01)
    *C11D 11/00*     (2006.01)
    *A61B 1/018*     (2006.01)
    *C11D 7/26*     (2006.01)
    *C11D 1/66*     (2006.01)
    *A61B 17/00*     (2006.01)

(52) U.S. Cl.
    CPC ............... *A61B 1/018* (2013.01); *C11D 1/74* (2013.01); *C11D 1/825* (2013.01); *C11D 7/265* (2013.01); *C11D 11/0041* (2013.01); *A61B 2017/00269* (2013.01); *C11D 1/667* (2013.01)

(56) References Cited

U.S. PATENT DOCUMENTS

| | | | |
|---|---|---|---|
| 4,767,617 A * | 8/1988 | Shansky | A61K 8/922 132/202 |
| 5,392,766 A * | 2/1995 | Masterson | A61B 1/0008 15/244.1 |
| 6,054,144 A * | 4/2000 | Burruano | A61K 9/145 424/464 |
| 6,059,407 A | 5/2000 | Komatsu et al. | |
| 6,193,986 B1 * | 2/2001 | Sakurada | A61K 9/10 424/400 |
| 2005/0119141 A1 | 6/2005 | Quenville et al. | |
| 2006/0293559 A1 * | 12/2006 | Grice, III | A61B 1/00135 600/102 |
| 2008/0292560 A1 * | 11/2008 | Tamarkin | A61K 8/046 424/45 |
| 2009/0041680 A1 * | 2/2009 | Tamarkin | A61K 8/86 424/45 |
| 2010/0004473 A1 * | 1/2010 | Kanaya | A61K 9/141 552/307 |
| 2010/0173394 A1 * | 7/2010 | Colston, Jr. | B01F 3/0807 435/287.2 |
| 2011/0182999 A1 * | 7/2011 | Serizawa | A61K 8/06 424/502 |
| 2013/0165528 A1 | 6/2013 | Wakita et al. | |
| 2015/0086701 A1 * | 3/2015 | Bot | A23D 7/0053 426/607 |
| 2015/0196027 A1 * | 7/2015 | Martin | A01N 37/02 514/461 |

FOREIGN PATENT DOCUMENTS

| | | |
|---|---|---|
| JP | 11-29793 | 2/1999 |
| JP | 2001-31999 | 2/2001 |
| JP | 2007-513654 | 5/2007 |
| JP | 2009-79084 | 4/2009 |
| JP | 2009-144070 | 7/2009 |
| JP | 2010-37512 | 2/2010 |
| JP | 2010-235801 | 10/2010 |
| JP | 2012-511394 | 5/2012 |
| JP | 2014-51444 | 3/2014 |
| WO | 2010/068265 | 6/2010 |
| WO | 2012/019023 | 2/2012 |

OTHER PUBLICATIONS

English translation of the International Preliminary Report on Patentability and Written Opinion dated Apr. 14, 2016 in corresponding International Application No. PCT/JP2014/075950.
Partial English translation of JP 1-159808, filed on Mar. 29, 2016.
Extended European Search Report dated Apr. 28, 2017 in corresponding European Application No. 14846871.3.
Database WPI, Section Ch, Week 201015 Thomson Scientific, London, GB; Class A25, AN 2010-B81201 XP002769240, Feb. 18, 2010.

\* cited by examiner

ENDOSCOPE LENS CLEANER

TECHNICAL FIELD

The present invention relates to a cleaner for cleaning various types of medical endoscopes, including laryngoscopes, bronchoscopes, upper gastrointestinal endoscopes, lower gastrointestinal endoscopes, duodenoscopes, enteroscopes, colonoscopes, capsule endoscopes, thoracoscopes, laparoscopes, cystoscopes, cholangioscopes, arthroscopes, spinal endoscopes, angioscopes, epiduroscopes, magnifying endoscopes, ultrasonic endoscopes, side-viewing endoscopes, oblique-viewing endoscopes, etc. In particular, the present invention relates to a cleaner for cleaning such various types of endoscopes inside a living body during a surgical procedure.

The present invention also relates to an antifoulant useful for antifouling treatment of such an endoscope before use.

BACKGROUND ART

With today's highly advanced medical techniques, various organs in a human body can be diagnosed and treated using a medical endoscope without making large surgical incision. Endoscopic diagnosis and treatment are applied to, for example, nasal cavity, pharynx, larynx, esophagus, trachea, bronchus, upper and lower gastrointestinal tract, thorax, abdominal cavity, renal pelvis and ureter, bile duct, joints, spine, blood vessels, subdural space, etc. However, during endoscopic diagnostic and therapeutic procedures of these organs, debris composed of blood, body fluid, gastric juice, saliva and cell debris as well as of fatty tissue released by resection of the affected site accumulates on the lens and results in a blurred endoscopic view, which often becomes obstacles to carry out diagnosis and treatment.

The above problem is currently addressed by rinsing the lens with purified water from the endoscope system or an alternative means, but such a method is not effective enough for obtaining a clear endoscopic view. Accordingly, a physician has to stop the procedure to withdraw the endoscope outside the body for wiping the debris from the lens, and then reinsert line endoscope into the body to continue the diagnostic or therapeutic procedure. However, withdrawing the endoscope greatly increases the burden on the physician and the patient.

Cleaning of a medical endoscope is often performed, using a pH-neutral dish detergent or a cleaner containing a zwitterionic surfactant such as aminoethyl glycine hydrochloride. Some medical facilities use so-called electrolytic water (alkaline water, acidic water or weakly acidic water) produced by electrolysis of sodium chloride solution. As examples of other types of cleaners, Patent Literature 1 discloses a cleaner for an endoscope, comprising a nonionic surfactant and an enzyme, and Patent Literature 2 discloses a cleaning composition for medical devices, comprising a nonionic polymer, a nonionic surfactant, ethylenediaminetetraacetic acid and monoethanolamine. However, the cleaning ability of these cleaners is not effective enough for removing the debris from the lens.

Furthermore, most of cleaners with relatively strong cleaning ability are harmful to a living body. Residual cleaners on an endoscope after cleaning is not desirable even in a small amount. Moreover, such cleaners cannot be used to clean an endoscope inside a living body during a surgical procedure. Therefore there has been a demand for the development of an endoscope lens cleaner with high cleaning ability and high safety for use inside a living body.

An endoscope hood is sometimes attached to ensure a clear endoscopic view. An endoscope hood (attachment) is a cap to be attached to the distal end of an endoscope. An endoscope hood has regained attention as a necessary tool for magnification endoscopy and therapeutic endoscopy, which have recently been widely performed. Such an endoscope hood (attachment) also suffers from, the same problem as an endoscope lens. That is, debris composed of blood, body fluid, gastric juice, saliva and cell debris as well as of fatty tissue released by resection of the affected site accumulates on the hood and results in a blurred endoscopic view. Therefore, there has also been a demand for the development of an endoscope hood cleaner with high cleaning ability and high safety for use inside a living body.

CITATION LIST

Patent Literature

Patent Literature 1: JP 2001-031999 A
Patent Literature 2: JP 2009-144070 A

SUMMARY OF INVENTION

Technical Problem

The present invention was made in view of the above problems, An object of the present invention is therefore to reduce the burden on a physician and the patient in endoscopic diagnosis and treatment and to provide a cleaner to be used inside a living body during an endoscopic surgical procedure. Another object of the present invention is to provide a cleaner with a high ability to clean debris from an endoscope lens and/or an endoscope hood (attachment). A further object of the present invention is to provide an antifoulant useful for antifouling treatment of an endoscope and/or endoscopic accessories, such as an endoscope lens and/or an endoscope hood (attachment).

Solution To Problem

The inventors conducted extensive research to solve the above problems, and as a result found that a cleaner produced from particular cleaning components than are highly safe to a living body exhibits high cleaning effect on debris accumulated on an endoscope lens and/or an endoscope hood (attachment). Surprisingly, the inventors also found that a cleaner with, such components exhibits an excellent ability to prevent fouling of an endoscope lens and/or an endoscope hood (attachment) and that the cleaner thus can also be used as an antifoulant. The inventors made further study and completed the present invention.

That is, the present invention relates to the following.
(1) A cleaner for an endoscope, the cleaner being used inside a living body during an endoscopic surgical procedure.
(2) The cleaner of the above (1), comprising a surfactant.
(3) The cleaner of the above (1), comprising no surfactant.
(4) The cleaner of any one of the above (1) to (3), for removal of debris from an endoscope and/or endoscopic accessories (in particular, an endoscope lens and/or an endoscope hood (attachment)).
(5) The cleaner of the above (2) to (4), comprising (i) a nonionic surfactant with an HLB of 1 to 11 and (ii) a nonionic surfactant with an HLB of 11 to 20.
(6) The cleaner of any one of the above (1) to (5), comprising at least one type of a detergent builder.

(7) The cleaner of the above (1) to (8), which is delivered from a water nozzle, a forceps channel or a water-jet nozzle of an endoscope.

The present invention also includes a method for cleaning an endoscope and/or endoscopic accessories (in particular, an endoscope lens and/or an endoscope hood (attachment)) with the cleaner inside a living body during an endoscopic surgical procedure [or a method for cleaning an endoscope and/or endoscopic accessories (in particular, an endoscope lens and/or an endoscope hood (attachment)) to remove accumulated debris thereon (for example, blood, body fluid, gastric juice, saliva, cell debris, fatty tissue, etc.)].

The present invention also includes an antifoulant for antifouling treatment Of an endoscope and/or endoscopic accessories (in particular, an endoscope lens and/or an endoscope hood (attachment)). Unlike the above cleaner, the antifoulant is an agent (composition) that is applied to an endoscope or endoscopic accessories (in particular, an endoscope lens and/or an endoscope hood (attachment)) outside a living body before they are inserted into the body, thereby reducing or preventing the accumulation of debris on the endoscope or the endoscopic accessories inside the living body during an endoscopic surgical procedure.

The components of the antifoulant may be the same as those contained in the above cleaner. The antifoulant may typically comprise (i) a nonionic surfactant with an HLE of 1 to 11 and (ii) a nonionic surfactant with an RLE of 11 to 20.

The antifoulant may further comprise an antifoulant builder (such as the same components as those used as detergent builders, for example, sodium, hydrogen carbonate).

The present invention also includes a method for subjecting an endoscope and/or endoscopic accessories (in particular, an endoscope lens and/or an endoscope hood (attachment)) to antifouling treatment with the antifoulant [or a method for reducing or preventing the accumulation of debris (for example, blood, body fluid, gastric juice, saliva, cell debris, fatty tissue, etc.) on an endoscope and/or endoscopic accessories (in particular, an endoscope lens and/or an endoscope hood (attachment)) inside a living body during an endoscopic surgical procedure, the -method comprising subjecting the endoscope and/or the endoscopic accessories to antifouling treatment before the surgical procedure].

The method may be combined with the above cleaning method. That is, the above methods may be a combined method comprising subjecting an endoscope and/or endoscopic accessories (in particular, an endoscope lens and/or an endoscope hood (attachment)) to antifouling treatment with the antifoulant before use, and then cleaning the endoscope and/or the endoscopic accessories (in particular, the endoscope lens and/or the endoscope hood (attachment)) inside a living body during an endoscopic surgical procedure [or a method for preventing the accumulation of debris on an endoscope and/or endoscopic accessories (in particular, an endoscope lens and/or an endoscope hood (attachment)) and removing debris inside a living body during an endoscopic surgical procedure, the method comprising cleaning the endoscope and/or the endoscopic accessories before and during the surgical procedure].

The endoscopic surgical procedure in the present invention (in particular, in use of the cleaner or the cleaning method, or the antifoulant or the antifouling treatment method) is not particularly limited, and may be, for example, endoscopic mucosal resection (EMR) or endoscopic submucosal dissection (ESD).

ESD is a surgical operation for tumors located in sites inaccessible to resection by SMR or for large tumors. ESD requires longer hours of operation and is thus more susceptible to the accumulation of debris. Hence the present invention may be appropriately used in, in particular, ESD.

Advantageous Effects of Invention

The present invention provides a cleaner that is highly safe for use inside a living body so that the cleaner can be used inside a living body during an endoscopic surgical procedure. The cleaner of the present invention has a high ability to clean debris from an endoscope and/or endoscopic accessories (in particular, from an endoscope lens and/or an endoscope hood) and provides antifogging effect to an endoscope lens. The present invention also provides an antifoulant useful for antifouling treatment of an endoscope and/or endoscopic accessories (in particular, an endoscope lens and/or an endoscope hood (attachment)) outside a living body before they are inserted into the body for an endoscopic surgical procedure. The antifoulant has excellent antifouling ability and reduces or prevents the accumulation of debris on an endoscope lens and/or an endoscope hood (attachment). The present invention greatly reduces the burden on a physician and the patient during an endoscopic surgical procedure.

DESCRIPTION OF EMBODIMENTS

The present invention will be described in detail below.
Cleaner

The present invention relates to a cleaner for an endoscope, the cleaner being used inside a living body during an endoscopic surgical procedure. The term "endoscopic surgical procedure" herein includes any types of diagnosis, treatment and prevention using an endoscope. The cleaner of the present invention comprises a cleaning component in such a manner that high safety for use inside a living body is ensured and that the cleaner exhibits a sufficient ability to clean debris from an endoscope lens and/or an endoscope hood (attachment). The cleaning component is not particularly limited, and the cleaner may comprise various types of known cleaning components. Such cleaning components can also be used as antifouling components as described later.

The cleaner of the present invention may comprise a surfactant, but it is not essential.

The cleaner of the present invention may comprise, if desired, one or more of a detergent builder (hereinafter also called a builder), a preservative, a solubilizing agent or an emulsifier, a viscosity modifier and an antioxidant.

The builder is not particularly limited, and may be an inorganic builder or an organic builder.

Specific examples of the inorganic builder include carbonates, sulfates, hydrochlorides, phosphates, and borates of alkali metals and alkaline earth metals and boric acid. More specific examples thereof include sodium hydroxide, sodium sulfate, magnesium sulfate, sodium chloride, magnesium chloride, carbonates (such as sodium carbonate), hydrogen carbonates (such as sodium hydrogen carbonate), phosphates (such as sodium phosphate, sodium monohydrogen phosphate, sodium dihydrogen phosphate, dipotassium phosphate, and potassium dihydrogen phosphate), sodium tripolyphosphate, sodium pyrophosphate, potassium pyrophosphate, sodium hexametaphosphate, borax, boric acid, magnesium carbonate, calcium carbonate, and calcium sulfate. Of these, preferred are sodium hydrogen carbonate, sodium phosphate, sodium monohydrogen phosphate, and potassium dihydrogen phosphate due to their ability to increase the cleaning effect.

Specific examples of the organic builder include carboxylic acids, hydroxycarboxylic acids, polycarboxylic acids, hydroxypolycarboxylic acids and salts thereof, and aminocarboxylic acids, aminopolycarboxylic acids, and salts thereof, each having 2 to 10 carbon atoms. More specific examples thereof include organic acids such as citric acid, malic acid, succinic acid, maleic acid, fumaric acid, gluconic acid and adipic acid and salts thereof and aminopolycarboxylic acids such as ethylenediaminetetraacetic acid and nitrilotriacetic acid and salts thereof. Examples of the organic builder further include sugars such as glucose, sucrose, fructose, and lactose; and ureas.

In an embodiment of the present invention, these builders can be used alone or in combination of two or more of them. In addition to their roles as a detergent builder, the builders can also serve as a pH adjuster. The builders (detergent builders) can also be used as an antifouling component (or an antifoulant builder) as described later, The amount of the builder(s) contained in the cleaner is not particularly limited, and may be, for example, typically less than 3% by mass based on the total mass of the cleaner, and to sufficiently achieve the intended effects, the amount is preferably 0.01 to 0.6% by mass and more preferably 0.05 to 0.3% by mass.

The preservative is not particularly limited and examples thereof include benzoic acid and salts thereof, salicylic acid and salts thereof, sorbic acid and salts thereof, denydroacetic acid and salts thereof, p-hydroxybenzoic acid esters such as p-hydroxybenzoic acid alkyl esters (e.g., methylparaben, ethylparaben, propylparaben, butylparaben, etc.), 2,4,4'-trichloro-2'-hydroxydiphenyl ether, 3,3,4'-trichlorocarbanilide, hexachlorophene, benzalkonium chloride, phenoxyethanol, hinokitiol, resorcin, ethanol, 1,3-butylene glycol, isopropylrnethylphenol, and polyhydric alcohols such as 1,3-butylene glycol, 1,2-pentanediol, 1,2-hexanediol, and 1,2-octanediol, Examples of the salts include sodium salts, potassium salts, magnesium salts, calcium salts, and ammonium salts. Of the above preservatives, methylparaben, propylparaben, ethanol, etc. are preferred in view of safety to a living body.

The solubilizing agent or the emulsifier is not particularly limited and examples thereof include dimethyIisosorbide, transcutol, ethyl alcohol, isopropyl alcohol, polyethylene glycol, propylene glycol, castor oil, isopropyl, myristate, octyldodecanol, isocetyl alcohol, oleyl alcohol, oleyl cetyl alcohol; triglycerides of medium-chain fatty acids derived from plants, such as caprylic triglyceride and capric triglyceride, Miglyols(R), which is a mixture of propylene glycol dicaprylate and propylene glycol dicaprate, Neobee M-5, which is a mixture of caprylic triglyceride and capric triglyceride; polysorbates such as polysorbate 20, polysorbate 40, polysorbate 60, and polysorbate 80; sorbitans such as sorbitan laurate, sorbitan oleate, sorbitan palmitate, sorbitan stearate, sorbitan trioleate, and sorbitan tristearate; glyceryl monostearate, polyoxyethylene stearate, polyoxyethylene lauryl ether, PEG-20 glyceryl stearate, ceteareth-12, ceteareth-20, ceteareth-30, PFG-2-ceteareth-9; polyethylene glycol ethers of oleyl alcohol, such as oleth-5, oleth-10, and a mixture of oleth-5 and oleth-10; stearols such as soya stearol, PEG-5 soya stearol, PEG-10 stearol, PEG-16 soya stearol, and PEG-25 soya stearol; sodium stearyl sulfate, PEG-40 hydrogenated castor oil, PEG-60 hydrogenated castor oil, and polyoxyethylene (160) polyoxypropylene (30) glycol. These solubilizing agents or emulsifiers may be used alone or in combination of two or more of them.

The viscosity modifier is not particularly limited and examples thereof include cetyl alcohol, stearyl alcohol, cetyl stearyl alcohol, myristyl alcohol, xanthan gum, VEEGUM (magnesium aluminum silicate), carbomer, glyceryl stearate, hydrogenated castor oil, cetyl palmitate, stearic acid, a combination of synthetic and semisynthetic wax, a combination of glyceryl stearate, stearyl alcohol, cetyl palmitate, and cocoglycerides blend, and a combination of glyceryl hydroxystearate, cetyl palmitate, and trihydroxystearin blend. These viscosity modifiers may be used alone or in combination of two or more of them.

The antioxidant used in the present invention is not particularly limited and examples thereof include ascorbic acid, phosphate derivatives of ascorbic acid, and salts thereof, stearic acid esters, tocopherol and derivatives thereof, butylated hydroxytoluene (BHT), butylated hydroxyanisole (BHA), hydroxytyrosol, p-hydroxyanisole, propyl gallate, sesamol, sesamolin, and gossypol.

The solvent used for the production of the cleaner of the present invention is not particularly limited and examples thereof include water, and lower alcohols, ether alcohols, glycols and ketones, each of which has 1 to 6 carbon atoms, such as methanol, ethanol, propanol, isopropyl alcohol, ethylene glycol, propylene glycol, diethylene glycol, methyl glycol, ethyl glycol, butyl glycol, glycerol, concentrated glycerol, acetone, and methyl ethyl ketone. The water may be tap water, purified water, sterile purified water, or sterile water. Of these solvents, water, in particular, purified water, sterile purified water, and sterile water are preferred in view of safety to a living body.

The pH of the cleaner of the present invention is not particularly limited, and may be, for example, typically 3 to 12, and is preferably 4 to 10 and more preferably 6 to 9, in view of safety to a living body and in order to enhance the cleaning effect.

The viscosity of the cleaner of the present invention is not particularly limited, and may be, for example, typically 1 to 500 mPa·s, and is preferably 1 to 200 mPa·s in view of clinical convenience.

One embodiment, of the present invention relates to the cleaner comprising a surfactant as a cleaning component. The surfactant used in the present invention may he any surfactant as long as the effects of the present invention are achieved. The surfactant may be, for example, a combination of nonionic surfactants with different HLBs values.

The hydrophile-lipophile balance (HLB) herein is an index indicating the hydrophilicity of a nonionic surfactant.

The HLB value can be calculated by any of the following formulas:

[(molecular weight of hydrophilic group moieties/molecular weight of surfactant)×100/5],

[(weight of hydrophilic groups/(weight of hydrophobic groups +weight of hydrophilic groups))×100/5], or

[(percent by weight of hydrophilic groups)×1/5].

The HLB value ranges from 0 to 20, and an HLB value closer to 20 indicates higher hydrophilicity.

In a preferred embodiment of the present invention, the cleaner comprises (i) a nonionic surfactant with an HLB of 1 to 11 and (ii) a nonionic surfactant with an HLB of 11 to 20 (for example, 12 to 19, preferably 13 to 18).

The nonionic surfactant (i) is not particularly limited and examples thereof include the following (the numbers in the brackets ([ ]) represent the HLB values): monoglyceride [2.6 to 3,5], sorbitan monocaprylate [9.6], sorbitan monolaurate [8.6], sorbitan monopalmitate [6.7], sorbitan monostearate [4.7], sorbitan monooleate [4.3], sorbitan trioleate [1.8], sorbitan trioleate with 20 mol EO [11.0], sorbitan monooleate with 5 mol EO [10.0], sorbitan monostearate with 4 mol EO [9.6], polysorbate 65 [10.5], polyethylene glycol (200) monolaurate [9.8], polyethylene glycol (200) monostearate [8.5], polyethylene glycol (200) monooleate [8.4], polyethylene glycol (200) dilaurate [6.6], polyethylene glycol (400) dilaurate [9.8], polyethylene glycol (200) distearate [5.4], polyethylene, glycol (400) distearate [8.5], polyethylene glycol (200) dioleate [5.3], polyethylene glycol (400) dioleate [8.4], polyethylene glycol (600) distearate [10.5], polyethylene glycol (600) dioleate [10.4], oleyl alcohol with 2 mol EO [4.9], whale alcohol with 5 mol EO [9.3], whale alcohol with 7 mol EO [10.8], nonylphenol with 4 mol EO [8.9], nonylphenol with 6 mol EO [10.9], lauryl alcohol with 5 mol EO [10.8], diglycerol monocaprylate [8.7], tetraglycerol monooleate [8.8], tetraglycerol monolaurate [10.3], sucrose stearate [1 to 11], sucrose laurate [1 to 5], and sucrose behenate [3]. These surfactants may be used alone or in combination of two or more of them. Of these surfactants, in view of safety to a living body, preferred are diglycerol monocaprylate [8.7], tetraglycerol monooleate [8.8], tetraglycerol monolaurate [10.3], sucrose stearate [1 to 1.11], sucrose laurate [1 to 5], sucrose behenate [3], etc.

The nonionic surfactant (ii) is not particularly limited and examples thereof include the following: sorbitan monolaurate with 4 mol EO [13.3], sorbitan monolaurate with 20 mol EO [16.7], sorbitan monopalmitate with 20 mol EO [15.6], sorbitan monostearate with 20 mol EO [14.9], sorbitan monooleate with 20 mol EO [15.0], polysorbate 20 [16.0 to 16.9], polysorbate 40 [15.6 to 16.0], polysorbate 60 [14.9 to 15.7], polysorbate 80 [15.0 to 15.7], polyethylene glycol (400) monolaurate [13.1], polyethylene glycol (600) monolaurate [14.8], polyethylene glycol (1000) monolaurate [16.5], polyethylene glycol (400) monostearate [11.9], polyethylene glycol (600) monostearate [13.8], polyethylene glycol (1000) monostearate [15.8], polyethylene glycol (400) monooleate [11.8], polyethylene glycol (600) monooleate [13.7], polyethylene glycol (1000) monooleate [15.7], polyethylene glycol (600) dilaurate [11.8], polyethylene glycol (1000) dilaurate [14.1], polyethylene glycol (1540) dilaurate [15.7], polyethylene glycol (1000) distearate [13.0], polyethylene glycol (1540) distearate [14.8], polyethylene glycol (1000) dioleate [12.9], polyethylene glycol (1540) dioleate [14.7], lauryl alcohol with 10 mol EO [14.1], lauryl alcohol with 23 mol EO [16.9], oleyl alcohol with 10 mol EO [12.4], oleyl alcohol with 20 mol EO [15.3], whale alcohol with 11 mol EO [13.2], whale alcohol with 14 mol EO [14.2], whale alcohol with 18 mol EO [15.1], whale alcohol with 24 mol EO [16.1], nonylphenol with 7 mol EO [11.7], nonylphenol with 10 mol EO [13.3], nonylphenol with 12 mol EO [14.1], nonylphenol with 14 mol EO [14.8], nonylphenol with 16 mol EO [15.2], nonylphenol with 20 mol EO [16.0], nonylphenol with 40 mol EO [17.8], decaglycerol monocaprylate [16.0], decaglycerol monolaurate [14.8], hexaglycerol monooleate [11.6], decaglycerol monolaurate [15.6], decaglycerol monomyristate [14.6], sucrose stearate [15 to 16], sucrose palmitate [15 to 16], sucrose myristate [16], sucrose oleate [15], and sucrose laurate [16]. These surfactants may be used alone or in combination of two or more of them. Of these surfactants, in view of safety to a living body, preferred are decaglycerol monocaprylate [16.0], decaglycerol monolaurate [14.8], hexaglycerol monooleate [11.6], decaglycerol monolaurate [15.6], decaglycerol monomyristate [14.6], sucrose stearate [15 to 16], sucrose palmitate [15 to 16], sucrose myristate [16], sucrose oleate [15], sucrose laurate [about 16], etc.

Herein EO represents ethylene oxide.

In a preferred embodiment of the present invention, the total amount of the nonionic surfactants contained in the cleaner is typically 0.1 to 40% by mass, preferably 1 to 35% by mass, more preferably 3 to 30% by mass, and particularly preferably 5% by mass or more (for example, 5 to 40% by mass, preferably 6 to 35% by mass, and further more preferably 7 to 30% by mass), based on the total weight of the cleaner. The cleaner containing the nonionic surfactants in such a total amount exhibits a sufficient cleaning effect and is sufficiently safe for use inside a living body.

The total amount of the surfactants may be appropriately selected depending on the combination of the surfactants to be used.

In another preferred embodiment of the present invention, the ratio of the nonionic surfactants (i):(ii) contained in the cleaner is, in terms of mass, typically 2:1 to 1:10, preferably 1:1 to 1:9, and more preferably 1:2 to 1:7. The cleaner containing the surfactants in such a ratio exhibits high cleaning effect.

in another preferred embodiment of the present invention, the combined HLB value of the nonionic surfactants (i) and (ii) is typically 11.1 to 16.0, preferably 13.0 to 15.5, and more preferably 13.6 to 15.3. The cleaner containing the surfactants with such a combined HLB value exhibits high cleaning effect.

Particularly preferably, the nonionic surfactants (i) and (ii) contained in the cleaner of the present invention has a combined HLB value of 13.6 to 15.3, a mass ratio (i):(ii) of 1:2 to 1:7, and a total amount of 3 to 30% by mass based on the total amount of the cleaner.

In a preferred embodiment of the present invention, it is preferred that the nonionic surfactant (i) is at least one type selected from the group consisting of diglycerol monocaprylate, tetraglycerol monooleate, and tetraglycerol monolaurate, and that the nonionic surfactant (ii) is at least one type selected from the group consisting of decaglycerol monocaprylate, decaglycerol monolaurate, hexaglycerol monooleate, decaglycerol monolaurate, and decaglycerol monomyristate.

The cleaner of the present invention comprising the surfactant (a) as a cleaning component may comprise, if desired, a builder, a preservative, a solubilizing agent or an emulsifier, a viscosity modifier, an antioxidant, a defoaming agent, etc. The builder, the preservative, the solubilizing agent or the emulsifier, the viscosity modifier, and the antioxidant may be the same as those described above. The solvent to be used and the viscosity and pH of the cleaner may also be the same as those described above.

The ratio of the detergent builder (for example, an inorganic builder such as sodium hydrogen carbonate) relative to 100 parts by mass of the surfactant(s) may be selected from the range of, for example, about 0.01 to 100 parts by mass (for example, about 0.03 to 50 parts by mass), and is preferably about 0.05 to 30 parts by mass, more preferably about 0.1 to 20 parts by mass, and particularly preferably about 0.5 to 20 parts by mass (for example, about 1 to 10 parts by mass).

The defoaming agent is not particularly limited and examples thereof include alcohols (such as methanol, ethanol, 1-propanol, 2-propanol, lauryl alcohol, and stearyl alcohol) and silicone compounds (such as dimethyl silicone, fluorosilicone, and polyether silicone). Of these defoaming agents, dimethyl silicone is preferred due to its defoaming performance and in view of safety to a living body.

Another embodiment of the present invention relates to the cleaner comprising no surfactant. In this embodiment, the components in the cleaner of the present invention are not particularly limited, and the cleaner may comprise, as a cleaning component, for example, an inorganic compound such as a carbonate, a sulfate, a hydrochloride, a phosphate or a borate of an alkali metal or an alkaline earth metal, or boric acid; or an organic compound such as a carboxylic acid, a hydroxycarboxylic acid, a polycarboxylic acid or a hydroxypolycarboxylic acid, or a salt thereof, or an aminocarboxylic acid or an aminopolycarboxylic acid, or a salt thereof, each having 2 to 10 carbon atoms.

The inorganic compound used as a cleaning component is not particularly limited and specific examples thereof include sodium sulfate, magnesium sulfate, sodium chloride, magnesium chloride, sodium carbonate, sodium hydrogen carbonate, sodium phosphate, sodium monohydrogen phosphate, sodium dihydrogen phosphate, sodium tripolyphosphate, sodium pyrophosphate, potassium pyrophosphate, sodium hexametaphosphate, borax, boric acid, magnesium carbonate, calcium carbonate, and calcium sulfate.

The organic compound used as a cleaning component is not particularly limited and specific examples thereof include carboxylic acids, hydroxycarboxylic acids, polycarboxylic acids, hydroxypolycarboxylic acids and salts thereof, and aminocarboxylic acids, aminopolycarboxylic acids, and salts thereof, each having 2 to 10 carbon atoms. More specific examples thereof include organic acids such as citric acid, malic acid, succinic acid, maleic acid, fumaric acid, gluconic acid and adipic acid and salts thereof; and aminopolycarboxylic acids such as ethylenediaminetetraacetic acid and nitrilotriacetic acid and salts thereof. Examples of the organic compound further include sugars such as glucose, sucrose, fructose, and lactose; and ureas.

In the cleaner of the present invention comprising no surfactant, the above cleaning components may be used alone or in combination of two or more of them. In order to enhance the cleaning effect, two or more of the cleaning components are preferably used in combination. The combination of the cleaning components is not particularly limited and examples of thereof include a combination of sodium hydrogen carbonate and sodium hexametaphosphate and a combination of sodium hydrogen carbonate and sodium citrate. In the present invention, such a combination of the cleaning components may be used together with a surfactant.

In this embodiment, the total amount of the cleaning components contained in the cleaner is not particularly limited and may be, for example, 0.01 to 10% by mass based on the total amount of the cleaner of the present invention.

In cases where two or more of the cleaning components are used in combination, the blending ratio may be any ratio as long as the cleaning effect is sufficiently achieved, in cases where, for example, two types of the cleaning components are used in combination, the blending ratio in terms of mass may be 1:1 to 1:5.

In cases where the cleaner of the present invention comprises no surfactant, the cleaning component(s) preferably also serves as a buffering agent.

The cleaner of the present invention comprising no surfactant may further comprise, if desired, an alkali for the purpose of adjusting the pH. Examples of the alkali include sodium hydroxide, potassium hydroxide, lithium hydroxide, sodium carbonate, potassium carbonate, ammonium carbonate, and a combination thereof.

The cleaner of the present invention comprising no surfactant may comprise, if desired, a builder, a preservative, a solubilizing agent or an emulsifier, a viscosity modifier, an antioxidant, etc. The builder, the preservative, the solubilizing agent or the emulsifier, the viscosity modifier and the antioxidant may be the same as those described above. The solvent to be used and the viscosity and pH of the cleaner may also be the same as those described above.

Preferably, the cleaner of the present invention comprising no surfactant hardly foams during cleaning even without the addition of a defoaming agent.

Figure 1:
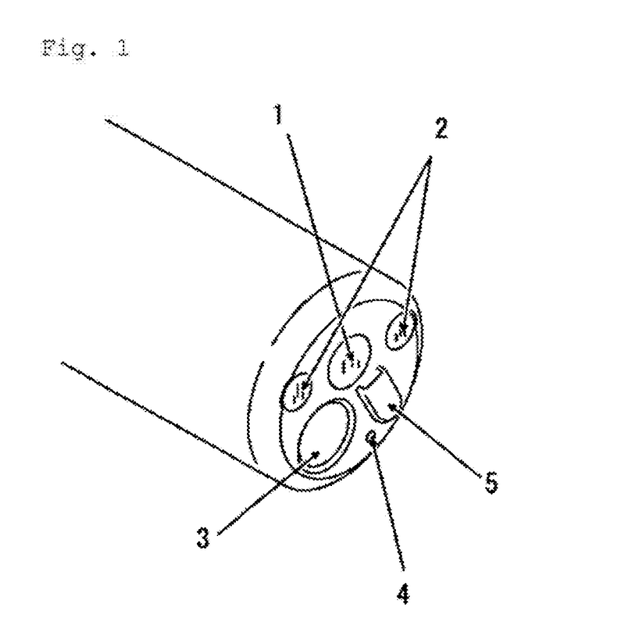
FIG. 1 is a schematic view of the distal end (with a lens) of an endoscope.

The cleaner of the present invention (comprising or not comprising a surfactant) is suitable for the removal of debris accumulated on an endoscope and/or endoscopic accessories (in particular, an endoscope lens and/or an endoscope hood (attachment)) inside a living body during an endoscopic surgical procedure. The delivery of the cleaner for the removal of debris from an endoscope lens can be done by any means, including, for example, an air/water nozzle (hereinafter simply called, "a water nozzle", see numeral 5 in FIG. 1), a forceps channel (see numeral 3 in FIG. 1), a water-jet nozzle (see numeral 4 of FIG. 1), etc. of an endoscope. The delivery means may be appropriately selected depending on the purpose.

Figure 2:
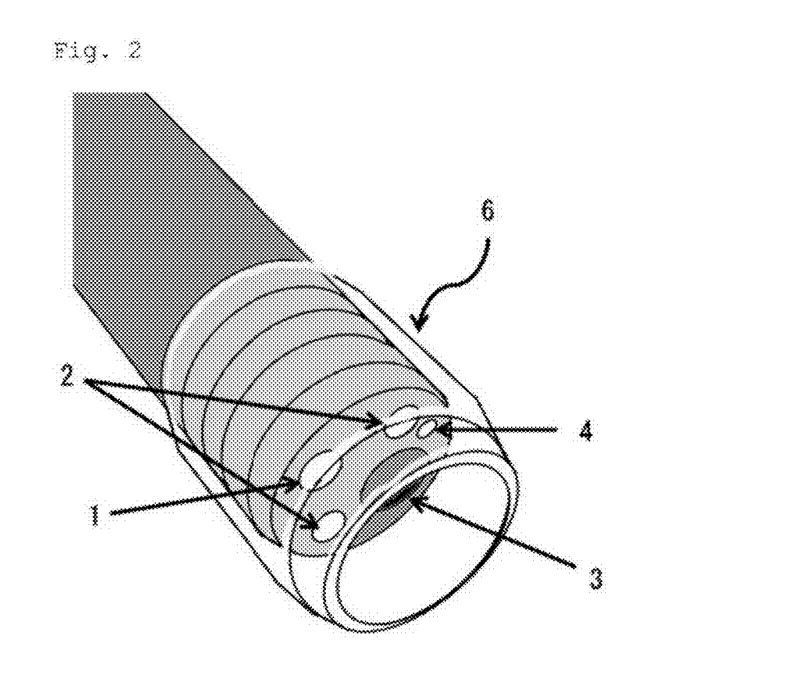
FIG. 2 is a schematic view of the endoscope distal end with an attached endoscope hood.

The endoscope hood (attachment) in the present invention is not particularly limited, and may be, for example, an attachment that is attached to an endoscope as shown in numeral 6 of the schematic view in FIG. 2. The material, color, shape, etc. of the endoscope hood may be appropriately selected as desired. Specific examples of the endoscope hood (attachment) include slit & hole type or straight type of Elastic Touch (registered trademark) made by Top Corporation; various types of hoods of Mole Cap (registered trademark) made by Top Corporation; etc.

In an embodiment of the present invention where a hood is attached to an endoscope, the removal of debris from the endoscope lens and the endoscope hood (attachment) is preferably done by, for example, spraying the cleaner on the endoscope hood (attachment) from a spray nozzle etc. inserted through the forceps channel. The spray nozzle is not particularly limited, and specific examples thereof include the spray nozzle of Fine Jet (registered trademark) made by Top Corporation, etc. More preferably, the removal of debris is done by, for example, deflecting the distal end upward with its face up and injecting the cleaner from the forceps channel so that the cleaner is kept in the endoscope hood (attachment) (i.e., the endoscope lens is kept immersed in the cleaner); or pressing the edge of the endoscope hood (attachment) against the inner wall of a cavity of a living body and injecting the cleaner so that the hood is filled with the cleaner. In this embodiment, the cleaner kept in the hood may be stirred with, for example, a stirring stick etc. inserted through the forceps channel.

In addition to the cleaning function, the cleaner of the present invention after used to remove the debris from an endoscope lens and/or an endoscope hood (attachment) also exhibits a function of providing antifogging effect to the endoscope lens and/or the endoscope hood (attachment).

With the use of the cleaner of the present invention, a physician can remove debris from an endoscope lens and/or an endoscope hood (attachment) during a surgical procedure without withdrawing the endoscope outside the body. The physician does not need to stop the procedure, and consequently the burden on the physician and the patient is greatly reduced.

Antifoulant

The cleaner (or its components) of the present invention can also be used as an antifoulant (a surface treating agent, an antifouling treatment agent, or a surface protective agent) for an endoscope and/or endoscopic accessories (or endoscope attachments), in particular, for an endoscope lens and/or an endoscope hood (attachment).

That is, an endoscope lens and/or an endoscope hood, etc. may be subjected to antifouling treatment using the cleaner (or its components) as an antifoulant [i.e., antifouling treatment in which, for example, the cleaner is applied to an endoscope lens and/or an endoscope hood (or the cleaner is allowed to adhere thereto)] outside a living body before the endoscope is inserted into the body. This antifouling treatment reduces or prevents the accumulation of various debris components (for example, fat etc.) on the endoscope lens and/or the endoscope hood (attachment), etc. inside the living body during an endoscopic surgical procedure.

The antifoulant can also provide antifogging effect to an endoscope lens and/or an endoscope hood (attachment), etc. Therefore, the antifoulant of the present invention can also be used as an antifogging agent (an antifouling and antifogging agent).

The components of the antifoulant may be the same as those of the above cleaner, and their content ratios are the same as described above. Among the above-described cleaning components, a surfactant is particularly suitable as an antifouling component.

The antifoulant may comprise, as an antifouling component, the above-described surfactant, for example, a surfactant combination of (i) a nonionic surfactant with an HLB of 1 to 11 and (ii) a nonionic surfactant with an HLB of 11 to 20 (for example, 12 to 19, preferably 13 to 18). The total amount of the nonionic surfactants may be typically 0.1 to 40% by mass, and is preferably 1 to 35% by mass, more preferably 3 to 30% by mass, and particularly preferably 5% by mass or more (for example, 5 to 40% by mass, preferably 6 to 35% by mass, and further more preferably 7 to 30% by mass), based on the total weight of the antifoulant.

The ratio of the nonionic surfactants (i):(ii) contained in the antifoulant may be, in terms of mass, typically 2:1 to 1:10, preferably 1:1 to 1:9, more preferably 1:2 to 1:7. The combined HLB value of the nonionic surfactants (i) and (ii) may be typically 11.1 to 16.0, and is preferably 13.0 to 15.5, and more preferably 13.6 to 15.3. The nonionic surfactants (i) and (ii) contained in the antifoulant of the present invention may have a combined HLB value of 13.6 to 15.3, a mass ratio of 1:2 to 1:7, and a total amount of 3 to 30% by mass based on the total amount of the cleaner.

The antifoulant may comprise the above-described builder (sodium hydrogen carbonate etc.) as an antifoulant builder. In this case, the ratio of the antifoulant builder relative to 100 parts by mass of the surfactant(s) can be selected from the range of about 0.01 to 100 parts by mass (for example, about 0.03 to 50 parts by mass), and is preferably about 0.05 to 30 parts by mass, more preferably about 0.1 to 20 parts by mass, and in particular may be about 0.5 to 20 parts by mass (for example, about 1 to 10 parts by mass).

That is, the antifoulant of the present invention may be the same as the above cleaner in terms of the components, their ratios, etc., except for its use in which the antifoulant is applied to an endoscope and/or endoscopic accessories (in particular, an endoscope lens and/or an endoscope hood (attachment)) outside a living body. Therefore, the above description of the components, their ratios, etc. regarding the cleaner can be applied to the antifoulant, by replacing the terms "cleaner" and "cleaning" with the terms "antifoulant" and "antifouling", respectively.

The application of the antifoulant (antifouling treatment) can be done by any method as long as the antifoulant is applied to or allowed to adhere to an endoscope and/or endoscopic accessories (in particular, an endoscope lens and/or an endoscope hood (attachment)). Examples of the method include coating, spraying and immersion, but are not limited thereto.

EXAMPLES

Hereinafter, the present invention will be described in more detail with reference to Examples and Comparative Examples, but is not limited thereto. Various modifications can be made within the technical idea of the present invention by those who have ordinary skill in the art.

Examples 1 to 16

To purified water were added diglycerol monocaprylate, tetraglycerol monolaurate and/or decaglycerol monocaprylate according to the formulas in Table 1. The mixture was heated to 80° C. in a water bath while stirred with a stirrer. After the dissolution, the solution was cooled to 40° C. or less, then sodium hydrogen carbonate was added, and the mixture was stirred until sodium hydrogen carbonate was dissolved. After the dissolution, the solution was cooled to 30° C. or less, then a silicone resin emulsion (defoaming agent) previously diluted five-fold with purified water was added, and the mixture was stirred until the silicone resin emulsion was uniformly dissolved. Purified water was finally added to a total amount of 100 g to give a cleaner.

In Table 1, the unit of the numerical values in the formulas is gram (g). The same is applied to Tables 2 to 6.

Examples 17 to 26

To purified water were added sodium hydrogen carbonate and/or trisodium citrate dihydrate according to the formulas in Table 2, and the mixture was thoroughly stirred to give a cleaner.

Comparative Example 1

Purified water in an amount of 100 g was used as a cleaner.

Comparative Example 2 to 6

To purified water were added diglycerol monocaprylate, decaglycerol monocaprylate and/or polysorbate 80 according to the formulas in Table 3. The mixture was heated to 80° C. in a water bath while stirred with a stirrer. After the dissolution, the solution was allowed to cool down to room temperature. Purified water was added to a total amount of 100 g to give a cleaner.

Test Example 1 (Cleaning Effect on Oil Film on Glass Slides)

Test Method
1) Fatty tissue from a resected porcine stomach model is melted by heating, and 20 g of the obtained oil and 0.1 g of Oil Red are dissolved in 60 mL of chloroform.
2) In the oil film model solution of the above 1), glass slides are immersed for 2 seconds (the slides are divided into sets of three).
3) The slides are left at room temperature for 1 to 2 hours for drying and solidifying the oil, and then weighed (the amount of adhering oil: 14±2 mg).
4) In separate beakers, 70 ml of each of the cleaners, at 25±1° C., obtained in Examples 1 to 26 and Comparative Examples 1 to 6 is placed.
5) In the beakers of the above 2), the glass slides with the oil film formed in the above 3) are immersed for 1 minute.
6) In another beaker containing 75 mL of water, the glass slides are immersed for 1 minute with shaking (100 rpm).
7) After natural drying, the sets of the three slides are immersed in chloroform for dissolution of the oil film.

The volume is adjusted to 50 mL, and the absorbance is determined for the calculation of a cleaning rate.

Cleaning Rate Calculation Method

Cleaning rate (%)=(absorbance after washed with purified water)/(absorbance after washed with cleaner)×100

Test Example 2 (Stability Test of Cleaners)

Test Method
Into separate vials, 50 mL of each of the cleaners obtained in Examples 1 to 26 and Comparative Examples 2 to 6 was poured. After sealing, the vials were stored at 5° C. or 40° C. for one month.

Evaluation Criteria
Good: clear homogeneous liquid without separation or precipitation.
Fair: cloudy homogeneous liquid without separation or precipitation.
Poor: inhomogeneous liquid with complete separation or precipitation.

The results of Test Examples 1 and 2 are shown in Tables 1 to 3.

All the cleaners of the Examples showed higher cleaning rates as compared with the cleaners of Comparative Examples 1 to 6. In particular, the cleaners of Examples 7 to 15 and Examples 17 to 26 showed excellent one-month storage stability at 5° C. and 40° C.

TABLE 1

| Component | Substance | HLB | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|---|---|
| Cleaner (nonionic surfactant) | Diglycerol monocaprylate | 8.7 | 0.25 | 0.5 | 1 | 2 | 3 | 3 | 3 | 3 | 3 |
| | Tetraglycerol monolaurate | 10.3 | | | | | | | | | |
| | Decaglycerol monocaprylate | 16.0 | 0.5 | 1 | 2 | 4 | 3 | 6 | 9 | 12 | 15 |
| Solubilizing agent | Polysorbate 80 | 15.7 | | | | | | | | | |
| Alkali metal salt or alkaline earth metal salt | Sodium hydrogen carbonate | — | | | | | | | | | |
| | Trisodium citrate dihydrate | — | | | | | | | | | |
| Defoaming agent | Silicone resin emulsion | — | | | | | | | | | |
| Solvent | Purified water | — | (q.s.) | (q.s.) | (q.s.) | (q.s.) | (q.s.) | (q.s.) | (q.s.) | (q.s.) | (q.s.) |
| Combined HLB of surfactants | | | 13.6 | 13.6 | 13.6 | 13.6 | 12.4 | 13.6 | 14.2 | 14.5 | 14.8 |
| Cleaning rate (%) | | | 132 | 133 | 121 | 170 | 124 | 328 | 319 | 435 | 381 |
| Stability (one month) | | 5° C. | Poor | Fair | Fair | Good | Good | Good | Good | Good | Good |
| | | 40° C. | Poor | Fair | Fair | Poor | Poor | Fair | Good | Good | Good |

| Component | Substance | HLB | Ex. 10 | Ex. 11 | Ex. 12 | Ex. 13 | Ex. 14 | Ex. 15 | Ex. 16 |
|---|---|---|---|---|---|---|---|---|---|
| Cleaner (nonionic surfactant) | Diglycerol monocaprylate | 8.7 | 3 | 3 | 1 | 1 | 2 | 2 | |
| | Tetraglycerol monolaurate | 10.3 | | | | | | | 7 |
| | Decaglycerol monocaprylate | 16.0 | 21 | 27 | 7 | 7 | 14 | 14 | 14 |
| Solubilizing agent | Polysorbate 80 | 15.7 | | | | | | | |
| Alkali metal salt or alkaline earth metal salt | Sodium hydrogen carbonate | — | | | | 0.1 | 0.2 | 0.2 | |
| | Trisodium citrate dihydrate | — | | | | | | | |
| Defoaming agent | Silicone resin emulsion | — | | | | | | 0.015 | |
| Solvent | Purified water | — | (q.s.) | (q.s.) | (q.s.) | (q.s.) | (q.s.) | (q.s.) | (q.s.) |
| Combined HLB of surfactants | | | 15.1 | 15.3 | 15.1 | 15.1 | 15.1 | 16.0 | 14.1 |
| Cleaning rate (%) | | | 207 | 169 | 169 | 435 | 183 | 216 | 479 |
| Stability (one month) | | 5° C. | Good | Good | Good | Good | Good | Good | Poor |
| | | 40° C. | Good | Good | Good | Good | Good | Good | Poor |

Ex.: Example

TABLE 2

| Component | Substance | HLB | Ex. 17 | Ex. 18 | Ex. 19 | Ex. 20 | Ex. 21 | Ex. 22 | Ex. 23 | Ex. 24 | Ex. 25 | Ex. 26 |
|---|---|---|---|---|---|---|---|---|---|---|---|---|
| Cleaner (nonionic surfactant) | Diglycerol monocaprylate | 8.7 | | | | | | | | | | |
| | Tetraglycerol monolaurate | 10.3 | | | | | | | | | | |
| | Decaglycerol monocaprylate | 16.0 | | | | | | | | | | |
| Solubilizing agent | Polysorbate 80 | 15.7 | | | | | | | | | | |
| Alkali metal salt or alkaline earth metal salt | Sodium hydrogen carbonate | — | 0.2 | 0.5 | 1 | | | | 1 | 1 | 1 | 1 |
| | Trisodium citrate dihydrate | — | | | | 0.2 | 0.5 | 1 | 0.2 | 0.5 | 1 | 2 |
| Defoaming agent | Silicone resin emulsion | — | | | | | | | | | | |
| Solvent | Purified water | — | (q.s.) | (q.s.) | (q.s.) | (q.s.) | (q.s.) | (q.s.) | (q.s.) | (q.s.) | (q.s.) | (q.s.) |
| Combined HLB of surfactants | | | — | — | — | — | — | — | — | — | — | — |
| Cleaning rate (%) | | | 143 | 169 | 201 | 121 | 121 | 126 | 243 | 168 | 409 | 167 |
| Stability (one month) | | 5° C. | Good | Good | Good | Good | Good | Good | Good | Good | Good | Good |
| | | 40° C. | Good | Good | Good | Good | Good | Good | Good | Good | Good | Good |

Ex.: Example

TABLE 3

| Component | Substance | HLB | Com. Ex. 1 | Com. Ex. 2 | Com. Ex. 3 | Com. Ex. 4 | Com. Ex. 5 | Com. Ex. 6 |
|---|---|---|---|---|---|---|---|---|
| Cleaner (nonionic surfactant) | Diglycerol monocaprylate | 8.7 | | | | 3 | 3 | |
| | Tetraglycerol monolaurate | 10.3 | | | | | | |
| | Decaglycerol monocaprylate | 16.0 | | 5 | 15 | | | |
| Solubilizing agent | Polysorbate 80 | 15.7 | | | | 6 | 9 | 9 |
| Alkali metal salt or alkaline earth metal salt | Sodium hydrogen carbonate | — | | | | | | |
| | Trisodium citrate dihydrate | — | | | | | | |
| Defoaming agent | Silicone resin emulsion | — | | | | | | |
| Solvent | Purified water | — | 100 | (q.s.) | (q.s.) | (q.s.) | (q.s.) | (q.s.) |
| Combined HLB of surfactants | | | — | 16.0 | 16.0 | 13.4 | 14.0 | 15.7 |
| Cleaning rate (%) | | | 100 | 106 | 112 | 99 | 97 | 98 |
| Stability (one month) | | 5° C. | — | Good | Good | Poor | Good | Good |
| | | 40° C. | — | Good | Good | Poor | Poor | Good |

Com. Ex.: Comparative Example

Examples 27 and 28

To purified water were added sodium hydrogen carbonate and/or trisodium citrate dihydrate according to the formulas in Table 4, and the mixture was thoroughly stirred to give a cleaner.

Examples 29 and 30

To water were added diglycerol monocaprylate and decaglycerol monocaprylate according to the formulas in Table 4. The mixture was heated to 80° C. in a water bath while stirred with a stirrer. After the dissolution, the solution was allowed to cool down to room temperature. Purified water was added to a total amount of 100 g to give a cleaner.

Comparative Example 7

Purified water in an amount of 100 g was used as a cleaner.

Test Example 3 (Cleaning Effect on Oil Film on Endoscope Lenses)

Test Method

1) Fatty tissue from a resected porcine stomach model is melted by heating to recover oil.
2) A certain amount of the oil of the above 1) is applied to the surface of an endoscope lens in a dry state, and an image through the lens is taken.
3) The distal end of the endoscope is immersed in 10 mL of the cleaner of Example 27, Example 28, Example 29, Example 30, or Comparative Example 7 in a beaker for 60 seconds.
4) After air supply and aspiration are performed, an image through the lens is taken.
5) The photographs of the above 2) and 4) are compared for the evaluation of the cleaning effect.

TABLE 4

| Component | Substance | HLB | Com. Ex. 7 | Ex. 27 | Ex. 28 | Ex. 29 | Ex. 30 |
|---|---|---|---|---|---|---|---|
| Cleaner (nonionic surfactant) | Diglycerol monocaprylate | 8.7 | | | | 3 | 3 |
| | Decaglycerol monocaprylate | 16.0 | | | | 9 | 12 |
| Alkali metal salt or alkaline earth metal salt | Sodium hydrogen carbonate | — | | 1 | 3 | | |
| | Trisodium citrate dihydrate | — | | | 1 | | |
| Solvent | Purified water | — | 100 | (q.s.) | (q.s.) | (q.s.) | (q.s.) |
| Combined HLB of surfactants | | | — | — | — | 14.2 | 14.5 |

Com. Ex.: Comparative Example
Ex.: Example

Figure 3:
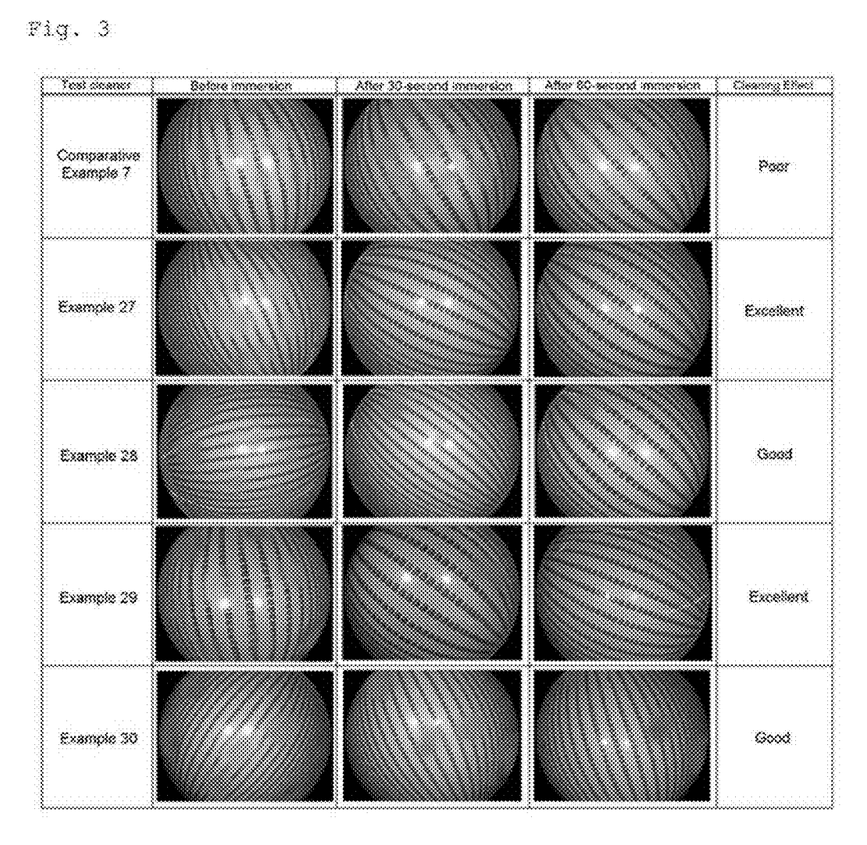
FIG. 3 shows the results of Test Example 3 (cleaning effect on oil film on endoscope lenses).

Evaluation Criteria
   Excellent: 90% or more of debris was removed.
   Good: 70% or more and less than 90% of debris was removed.
   Fair: 50% or more and less than 70% of debris was removed.
   Poor: Less than 50% of debris was removed.
   The results of Test Example 3 are shown in FIG. 3.
   Comparative Example 7 hardly removed the debris whereas all of the cleaners of Examples 27 to 30 showed high debris removal rates of 70% or more.

Examples 31 and 32

To water were added diglycerol monocaprylate and decaglycerol monocaprylate according to the formulas in Table 5. The mixture was heated to 80° C. in a water bath while stirred with a stirrer. After the dissolution, the solution was allowed to cool down to room temperature. Purified water was added to a total amount of 100 g to give a cleaner.

Comparative Example 8

Purified water in an amount of 100 g was used as a cleaner.

TABLE 5

| Component | Substance | HLB | Comparative Example 8 | Example 31 | Example 32 |
|---|---|---|---|---|---|
| Cleaner (nonionic surfactant) | Diglycerol monocaprylate | 8.7 | | 3 | 3 |
| | Decaglycerol monocaprylate | 16.0 | | 9 | 12 |
| Solvent | Purified water | — | 100 | (q.s.) | (q.s.) |
| Combined HLB of surfactants | | | — | 14.2 | 14.5 |

Test Example 4 (Cleaning Effect on Oil Film, on Endoscope Hoods (Attachments))

Figure 4:
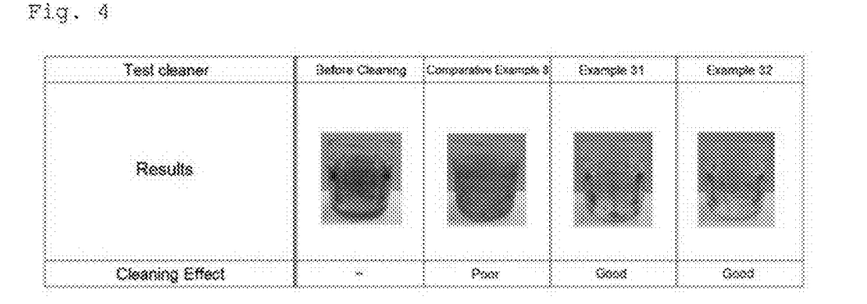
FIG. 4 shows the results of Test Example 4 (cleaning effect on oil film on endoscope hoods (attachments)).

Test Method
1) Fatty tissue from a resected porcine stomach model is melted by heating, and 20 g of the obtained oil and 0.1 g of Oil Red are dissolved in 60 mL of chloroform.
2) In the oil film model solution of the above 1), an endoscope hood (attachment) is immersed for 1 second, and a photograph of the hood is taken.
3) The hood of the above 2) is immersed in 20 mL of the cleaner of Example 31, Example 32, or Comparative Example 8 at 25±1° C. in a beaker for 1 second, and a photograph of the hood is taken.
4) The photographs of the above 2) and 3) are compared for the evaluation of the cleaning effect.
Evaluation Criteria
   Good: 70% or more of debris was removed.
   Fair: 50% or more and less than 70% of debris was removed.
   Poor: Less than 50% of debris was removed.
   The results of Test Example 4 are shown in FIG. 4.
   Both of Examples 31 and 32 showed high debris removal rates.

Examples 33 and 34

To purified water were added diglycerol monocaprylate and decaglycerol monocaprylate according to the formulas in Table 6. The mixture was heated to 80° C. in a water bath while stirred with a stirrer. After the dissolution, the solution was allowed to cool down to room temperature. Purified water was added to a total amount of 100 g to give a cleaner.

Comparative Example 9

Purified water in an amount of 100 g was used as a cleaner.

TABLE 6

| Component | Substance | HLB | Comparative Example 9 | Example 33 | Example 34 |
|---|---|---|---|---|---|
| Cleaner (nonionic surfactant) | Diglycerol monocaprylate | 8.7 | | 3 | 3 |
| | Decaglycerol monocaprylate | 16.0 | | 9 | 12 |
| Solvent | Purified water | — | 100 | (q.s.) | (q.s.) |
| Combined HLB of surfactants | | | — | 14.2 | 14.5 |

Test Example 5 (Antifogging Effect)

Figure 5:
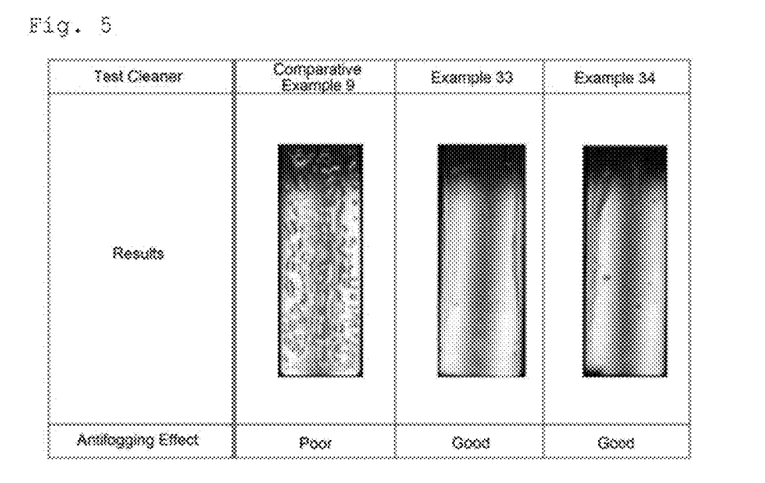
FIG. 5 shows the results of Test Example 5 (antifogging effect).

Test Method
1) On a glass slide, a drop of 50 μL of the cleaner (25±1° C.) obtained, in Example 33, Example 33, or Comparative Example 9 is placed, and spread over the entire surface.
2) The glass slide of the above 1) is held horizontal at 5° C./ambient humidity for 10 minutes.
3) The glass slide is transferred into a thermostatic chamber at 40° C./75% RH and held horizontal for 2 minutes.
4) Immediately after taking the glass slide out of the thermostatic chamber, the antifogging effect is evaluated at room temperature/ambient humidity and expressed as Good, Fair, or Poor.
Evaluation Criteria
   Good: Sufficient antifogging effect was observed.
   Fair: Slight antifogging effect was observed.
   Poor: No antifogging effect was observed.
   The results of Test Example 5 are shown in FIG. 5.
   Examples 33 and 34 showed high antifogging effect.

Example 35

Figure 6:
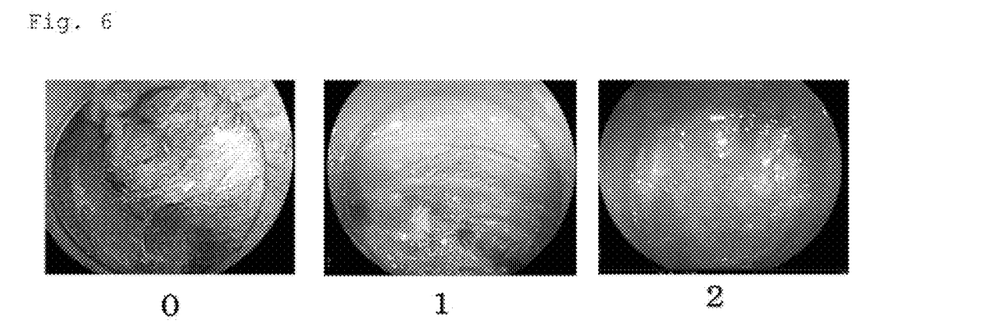
FIG. 6 shows endoscopic photographs used as an indicator for the evaluation of debris accumulated on the endoscope lens after endoscopic submucosal dissection.

Using the cleaner of Example 15 as an antifoulant, antifouling treatment was given to an endoscope lens. The anti fouling treatment was performed by applying the antifoulant to the surface of the endoscope lens with a cotton swab.
   Using the treated endoscope, endoscopic submucosal dissection (ESD) in patients with colon tumors was carried out in a conventional manner. Endoscopic images obtained after the submucosal dissection were observed and evaluated based on the following criteria.
Accumulation of Debris After Submucosal Dissection
   Grade 0: no debris was observed on the endoscope lens, or debris was perfectly removed by washing the lens inside the colon and rectum with water injected from the forceps channel or water delivered by the endoscope system (level 0 in FIG. 6).
   Grade 1: debris was not perfectly removed by the above-described washing with water but did not result in severely blurred endoscopic view (level 1 in FIG. 6).
   Grade 2: debris was not perfectly removed by the above-described washing with water and ESD could not be continued due to severely blurred endoscopic view (level 2 in FIG. 6).

Images of Fat in the Submucosal Adipose Tissue

Figure 7:
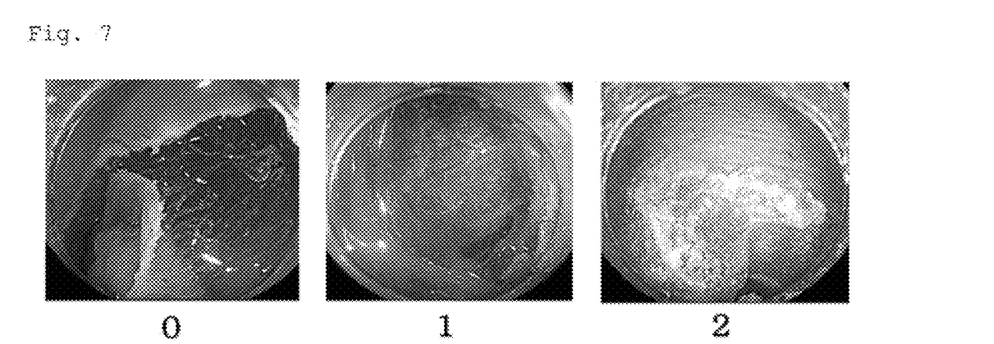
FIG. 7 shows endoscopic photographs used as an indicator for the evaluation of the amount of fat in the submucosal adipose tissue.

Grade 0: no fat in the adipose tissue (level 0 in FIG. 7).

Grade 1: a small amount of fat in the adipose tissue (level 1 in FIG. 7).

Grade 2: a large amount of fat in the adipose tissue, which made the dissection difficult to carry out (level 2 in FIG. 7).

The number of the patients was 92, the mean age was 68.3 (35 to 85 years, male/female (%)=51.0/49.0), the mean tumor size was 31.8 mm, and the mean procedure time was 71.1 minutes.

During the ESD, cloudiness of the lens was not observed.

Example 36

ESD was performed using an endoscope that was subjected to antifouling in the same manner as in Example 30 except for using, instead of the cleaner of Example 15, a commercially available endoscopic antifogging agent for use in natural orifice ("SL cleaner" made by Sugiura Laboratory, Inc.; components: linear alkylbenzene sulfonate (anionic surfactant), polyoxyethylene alkyl ether, and ethanol). Endoscopic images obtained during and after the submucosal dissection were observed and evaluated.

The number of the patients was 103, the mean age was 68.8 (41 to 92 years, male/female (%)=63.1/36.9), the mean tumor size was 32.7 mm, and the mean procedure time was 77.1 minutes. No significant difference was observed compared with the cases in Example 35 (p=NS).

The results obtained in Examples 35 and 36 are summarized in the following table. The "%" for each grade means the percentage out of all patients.

nel so that the cleaner was kept in the endoscope hood (attachment) for 30 seconds (i.e., the endoscope lens was kept immersed in the cleaner for 30 seconds).

The images through the lens after the cleaning were observed and evaluated based on the same criteria as in Example 35. All of the five cases with Grade 1 showed the results with Grade 0. Of the five cases with Grade 2, three cases showed the results with Grade 1 and the other two cases showed the results with Grade 0.

The results revealed that even for cases) with Grade 1 or 2 in terms of the accumulation of debris, the debris is easily removed with the cleaner of the present invention.

INDUSTRIAL APPLICABILITY

The present invention provides a cleaner for an endoscope, the cleaner being used inside a living body during an endoscopic surgical procedure. The cleaner of the present invention can be used to clean debris from an endoscope lens and/or an endoscope hood (attachment) inside a living body, which feature greatly reduces the burden on a physician and the patient during an endoscopic surgical procedure. The cleaner of the present invention improves the antifogging properties of an endoscope lens and/or an endoscope hood (attachment), and thereby increases the usability of an endoscopic surgical procedure.

The present invention also provides an antifoulant to be used for an endoscope lens and/or an endoscope hood (attachment) before an endoscopic surgical procedure. The

TABLE 7

| | Amount of fat in submucosal adipose tissue | | | | | Accumulation of debris after submucosal dissection | | | | |
|---|---|---|---|---|---|---|---|---|---|---|
| | Grade 0 (%) | Grade 1 (%) | Grade 2 (%) | Grade 1 + 2 (%) | p value | Grade 0 (%) | Grade 1 (%) | Grade 2 (%) | Grade 1 + 2 (%) | p value |
| Ex. 35 | 47.8 | 39.1 | 13.0 | 52.1 | NS | 85.9 | 12.0 | 2.1 | 14.1 | <0.01 |
| Ex. 36 | 51.5 | 39.8 | 8.7 | 48.5 | | 67.0 | 24.3 | 8.7 | 33.0 | |

Ex.: Example

As clearly shown in the table, the antifouling treatment successfully reduced the accumulation of debris on the endoscope lens after the ESD of the patients. In particular, the amount of fat in the submucosal adipose tissue in the patients was similar (not significant (NS)) between Example 35 and Example 36, but Example 35 using the antifoulant containing the specific surfactants as antifouling components significantly reduced the accumulation of debris on the endoscope lens compared with Example 36 using the commercially available endoscopic antifoulant for use in natural orifice.

Example 37

From the patients in Example 36, five cases determined as Grade 1 and five cases determined as Grade 2 in terms of the accumulation of debris after submucosal dissection were selected, and the cleaning effect of the cleaner of Example 15 on an endoscope lens (and an endoscope hood (attachment)) was further evaluated inside the bodies of these patients.

The cleaning was performed as follows. The distal end of the endoscope was deflected upward with its face up, and the cleaner of Example 15 was injected from the forceps chanantifoulant reduces or prevents the accumulation of debris on the endoscope lens and/or the endoscope hood (attachment).

REFERENCE SIGNS LIST

1 Objective lens
2 Light guides
3 Forceps channel
4 Water-jet nozzle
5 Air/water nozzle
6 Endoscope hood (attachment)

The invention claimed is:

1. An antifoulant for antifouling treatment of an endoscope lens and/or an endoscope hood, the antifoulant comprising (i) a first nonionic surfactant with an HLB of 1 to 10.9 and (ii) a second nonionic surfactant with an HLB of 11 to 20, wherein
the (i) first nonionic surfactant is at least one selected from the group consisting of diglycerol monocaprylate and tetraglycerol monolaurate, and
the (ii) second nonionic surfactant is at least one selected from the group consisting of decaglycerol monocaprylate, decaglycerol monolaurate and decaglycerol monomyristate.

2. The antifoulant of claim 1, further comprising an antifoulant builder.

3. The antifoulant of claim 1, wherein the ratio of the (i) first nonionic surfactant to the (ii) second nonionic surfactant ((i):(ii)) is, in terms of mass, 2:1 to 1:10.

4. A method for reducing or preventing accumulation of debris on an endoscope lens and/or an endoscope hood inside a living body during an endoscopic surgical procedure, the method comprising subjecting the endoscope lens and/or the endoscope hood to antifouling treatment with the antifoulant according to claim 1.

5. The method of claim 4, wherein the endoscopic surgical procedure is endoscopic mucosal resection or endoscopic submucosal dissection.

\* \* \* \* \*